(12) United States Patent
Law

(10) Patent No.: US 9,629,990 B2
(45) Date of Patent: Apr. 25, 2017

(54) APPLICATORS

(71) Applicant: Rieke Corporation, Auburn, IN (US)

(72) Inventor: Brian Robert Law, Leicester (GB)

(73) Assignee: Rieke Corporation, Auburn, IN (US)

( * ) Notice: Subject to any disclaimer, the term of this patent is extended or adjusted under 35 U.S.C. 154(b) by 88 days.

(21) Appl. No.: 14/552,634

(22) Filed: Nov. 25, 2014

(65) Prior Publication Data
US 2015/0078801 A1 Mar. 19, 2015

Related U.S. Application Data

(63) Continuation of application No. PCT/GB2013/051455, filed on May 31, 2013.

(30) Foreign Application Priority Data

May 31, 2012 (GB) .................................. 1209880.2

(51) Int. Cl.
*A61M 35/00* (2006.01)
*A61F 13/40* (2006.01)
*A61B 17/00* (2006.01)

(52) U.S. Cl.
CPC ........ *A61M 35/006* (2013.01); *A61M 35/003* (2013.01); *A61B 2017/00495* (2013.01)

(58) Field of Classification Search
CPC .. B05C 17/00586; B65D 51/20; B65D 51/22; B65D 51/221–51/227; B65D 81/3227;
(Continued)

(56) References Cited

U.S. PATENT DOCUMENTS 2,976,560 A 3/1961 Turner
2,998,822 A 9/1961 Birch et al.
(Continued)

FOREIGN PATENT DOCUMENTS

DE 20 2005 012686 U1 10/2005
WO WO 85/04794 A1 11/1985
(Continued)

OTHER PUBLICATIONS

International Search Report and Written Opinion for WO 2011/018621 dated Mar. 29, 2011.
(Continued)

*Primary Examiner* — Jennifer C Chiang
*Assistant Examiner* — Joshua Wiljanen
(74) *Attorney, Agent, or Firm* — Woodard Emhardt Moriarty McNett & Henry LLP

(57) ABSTRACT

A surgical preparation applicator device has a pre-loaded container of surgical preparation liquid, the container having a front closure at its front end. The container is received in an applicator body which includes a tubular receiving structure, movable from an initial position to an open position whereby a cutter of the applicator body opens the front closure to allow liquid to flow forwardly to an applicator pad. The applicator body defines a flow path between the container and the applicator pad. The container has separate chambers containing different component liquids of the surgical preparation liquid. The chambers are separated by an internal wall and being side-by-side, each having a front opening at the front end of the container with the front closure closing off both front openings.

7 Claims, 13 Drawing Sheets

(58) Field of Classification Search
CPC ............ B65D 81/3244; B65D 81/325; A61M 35/003; A61M 35/006
USPC ....... 401/16, 17, 22, 23, 132, 133, 134, 135, 401/148; 220/277, 278; 222/85, 86
See application file for complete search history.

(56) References Cited

U.S. PATENT DOCUMENTS

| | | | |
|---|---|---|---|
| 3,324,855 A | 6/1967 | Heimlich et al. |
| 3,349,966 A | 10/1967 | Schartzman |
| 3,399,020 A | 8/1968 | Margolis et al. |
| 3,519,364 A | 7/1970 | Truhan |
| 3,601,287 A | 8/1971 | Schwartzman |
| 3,636,922 A | 1/1972 | Ketner |
| 3,891,331 A | 6/1975 | Avery |
| 4,084,910 A | 4/1978 | LaRosa |
| 4,140,409 A | 2/1979 | DeVries |
| 4,148,318 A | 4/1979 | Meyer |
| 4,173,978 A | 11/1979 | Brown |
| 4,183,684 A | 1/1980 | Avery, Jr. |
| 4,201,491 A | 5/1980 | Kohler |
| 4,225,254 A | 9/1980 | Holberg et al. |
| 4,415,288 A | 11/1983 | Gordon et al. |
| 4,498,796 A | 2/1985 | Gordon et al. |
| 4,507,111 A | 3/1985 | Gordon et al. |
| 4,578,055 A | 3/1986 | Fischer |
| 4,863,422 A | 9/1989 | Stanley |
| 4,925,327 A | 5/1990 | Wirt |
| 5,006,004 A | 4/1991 | Dirksing et al. |
| 5,015,228 A | 5/1991 | Columbus et al. |
| 5,019,033 A | 5/1991 | Geria |
| 5,088,849 A | 2/1992 | Johnson et al. |
| 5,147,337 A | 9/1992 | Plone |
| 5,288,159 A | 2/1994 | Wirt |
| 5,308,180 A | 5/1994 | Pournoor et al. |
| 5,435,660 A | 7/1995 | Wirt |
| 5,445,462 A | 8/1995 | Johnson et al. |
| 5,489,280 A | 2/1996 | Russell |
| 5,509,744 A | 4/1996 | Frazier |
| 5,568,988 A | 10/1996 | Knox et al. |
| 5,658,084 A | 8/1997 | Wirt |
| 5,713,843 A | 2/1998 | Vangsness |
| 5,769,552 A | 6/1998 | Kelley et al. |
| 5,775,826 A | 7/1998 | Miller |
| 5,791,801 A | 8/1998 | Miller |
| 5,871,297 A | 2/1999 | Rogers et al. |
| 5,908,256 A | 6/1999 | Bernstein |
| 5,934,296 A | 8/1999 | Clay |
| 6,190,367 B1 | 2/2001 | Hall |
| 6,238,117 B1 | 5/2001 | Griebel et al. |
| 6,371,675 B1 | 4/2002 | Hoang et al. |
| 6,422,778 B2 | 7/2002 | Baumann et al. |
| 6,471,095 B1 | 10/2002 | Cann |
| 6,475,701 B2 | 11/2002 | Ohno et al. |
| 6,488,665 B1 | 12/2002 | Severin et al. |
| 6,505,985 B1 | 1/2003 | Hidle et al. |
| 6,533,484 B1 | 3/2003 | Osei et al. |
| 6,536,975 B1 | 3/2003 | Tufts |
| 6,595,696 B1 | 7/2003 | Zellak |
| 6,616,363 B1 | 9/2003 | Guillaume et al. |
| 6,672,784 B2 | 1/2004 | Baumann et al. |
| 6,689,103 B1 | 2/2004 | Palasis |
| 6,729,786 B1 | 5/2004 | Tufts et al. |
| 6,743,211 B1 | 6/2004 | Prausnitz et al. |
| 6,755,586 B1 | 6/2004 | Frazier |
| 6,773,193 B2 | 8/2004 | Delage |
| 6,805,682 B1 | 10/2004 | Campbell |
| 6,811,341 B2 | 11/2004 | Crane |
| 6,869,242 B2 | 3/2005 | May |
| 6,909,339 B2 | 6/2005 | Yonekura et al. |
| 6,910,822 B2 | 6/2005 | Hidle et al. |
| 6,916,133 B2 | 7/2005 | Hoang et al. |
| 6,916,137 B2 | 7/2005 | Shiraiwa |
| 6,991,394 B2 | 1/2006 | Tufts et al. |
| 7,090,422 B2 | 8/2006 | Baumann et al. |
| 7,201,525 B2 | 4/2007 | Mohiuddin |
| 7,261,701 B2 | 8/2007 | Davis et al. |
| 7,866,907 B2 | 1/2011 | Cable, Jr. et al. |
| 8,002,486 B1 | 8/2011 | Tran |
| 8,113,731 B2 | 2/2012 | Cable, Jr. et al. |
| 8,348,537 B2 | 1/2013 | Cable, Jr. et al. |
| 2001/0055511 A1 | 12/2001 | Baumann et al. |
| 2002/0076255 A1 | 6/2002 | Hoang et al. |
| 2002/0076258 A1 | 6/2002 | Crosby et al. |
| 2003/0049069 A1 | 3/2003 | Osei et al. |
| 2003/0060746 A1 | 3/2003 | Mark |
| 2003/0068190 A1 | 4/2003 | Hidle et al. |
| 2003/0118629 A1 | 6/2003 | Scholz et al. |
| 2003/0149106 A1 | 8/2003 | Mosbey et al. |
| 2003/0194447 A1 | 10/2003 | Scholz et al. |
| 2004/0068218 A1 | 4/2004 | Davis et al. |
| 2004/0114988 A1 | 6/2004 | Baumann |
| 2004/0162533 A1 | 8/2004 | Alley |
| 2004/0179888 A1 | 9/2004 | Tufts et al. |
| 2004/0240927 A1 | 12/2004 | Hoang et al. |
| 2004/0267182 A1 | 12/2004 | Davis et al. |
| 2006/0039742 A1 | 2/2006 | Cable et al. |
| 2006/0072962 A1 | 4/2006 | Cybulski et al. |
| 2007/0147947 A1 | 6/2007 | Stenton |
| 2007/0292193 A1 | 12/2007 | Lee et al. |
| 2009/0320856 A1 | 12/2009 | Brewer |
| 2011/0066121 A1* | 3/2011 | Hoang .................. A45D 34/04 604/310 |
| 2011/0284583 A1 | 11/2011 | Fazzolari |

FOREIGN PATENT DOCUMENTS

| | | |
|---|---|---|
| WO | WO 94/13352 A1 | 6/1994 |
| WO | WO 95/03734 | 2/1995 |
| WO | WO 99/51184 A1 | 10/1999 |
| WO | WO 00/10889 | 3/2000 |
| WO | WO 02/49708 A2 | 6/2002 |
| WO | WO 2004/062709 | 7/2004 |
| WO | WO 2006/131747 A1 | 12/2006 |
| WO | WO 2011/018621 | 2/2011 |

OTHER PUBLICATIONS

International Search Report and Written Opinion for WO 2011/018622 dated Jan. 27, 2011.

PCT/GB2013/051455 International Search Report dated Oct. 7, 2013.

* cited by examiner

APPLICATORS

CROSS-REFERENCE TO RELATED APPLICATIONS

This application is a continuation of International Application No. PCT/GB2013/051455 filed May 31, 2013, which claims the benefit of GB 1209880.2 filed May 31, 2012, which are hereby incorporated by reference.

FIELD OF THE INVENTION

The invention relates to applicators for applying surgical preparation or treatment liquids to skin, sometimes called surgical prep applicators.

BACKGROUND

The conventional preparation of a patient's skin for surgery includes an extended period of cleaning using soap or the like, followed by the application of an antiseptic or disinfectant. The nature, duration and difficulty of this task depend heavily on the kind of surgical procedure to be followed, and on the size, shape and orientation of the body parts involved.

The oldest—and still widespread—method of applying the disinfectant is by dipping a swab, sponge or pad, held in forceps, into a dish of liquid and wiping it over the skin. Spent swabs/pads are continually discarded and fresh ones taken. The disinfectant is usually alcohol-based and may contain ingredients (such as iodine) that can irritate or burn the skin. It is important that the rate of application of solution be controlled, so that excess does not flow away to unintended areas, or form pools underneath the body or in hollows of the body where it may burn or irritate the patient, or indeed be a fire hazard if a cauterisation procedure is used. It is generally desirable to avoid mess or spillage whether on the patient's body or elsewhere. Another reason for keeping the applied liquid under control is to avoid liquid which has contacted one region of the patient's skin flowing away (or being carried on the applicator) so that it then contacts another region.

Conversely, and despite all the above factors indicating careful application, surgical prep is often done under severe time pressure and subject to safety and effectiveness there is every interest in doing it as quickly as possible.

Over the years many proposals have been made for hand-held applicator devices for applying surgical prep solution, incorporating an applicator head with a pad, sponge or other soft or deformable permeable element to be wiped across the skin, and a reservoir of the surgical prep solution—often contained in a handle of the device—communicating with the applicator pad to feed solution. This can make the application more efficient by obviating the repeated dipping of swabs and the discarding and replacement of spent swabs. The solution can be provided in a sealed sterile reservoir or cartridge, which can be opened by engaging it appropriately with an applicator head (e.g. by a spike built into the applicator head rupturing a membrane or film closure on the front of the cartridge). Operation of these devices can be easier and neater compared with the use of swabs.

Surgical preparation solutions can desirably be a mixture of two or more components. Commonly, these components cannot be pre-mixed in the container liquid, as they may interact and degrade.

WO2011/018621 discloses a twin chamber system. The first chamber is provided in front of the second, and the chambers are opened successively. Such devices can be difficult to assemble and/or fill, and care must be taken to ensure that in use, the two components are well mixed, and that the solution is uniform over the dispensing lifetime of the applicator.

Many applicators previously used have liquid containers which must be broken or pierced to release the liquid. U.S. Pat. No. 4,415,288, U.S. Pat. No. 4,498,796 and U.S. Pat. No. 6,488,665 disclose applicators which use internal piercers to open the liquid container.

The openers of the applicators described above result in a portion of the container being broken off or a flap being cut loose. This broken portion or flap may cause a reduction or variation in the flow rate over the dispensing lifetime of the applicator. It is particularly important to have a consistent and known flow rate in a device in which component liquids are mixed after the container is opened. Otherwise, mixing of the multiple components may be non-uniform over the dispensing lifetime of the applicator.

The present application presents proposals for applicators using pre-loaded liquid containers, and for new kinds of pre-loaded container for use with such applicators, addressing the above issues.

SUMMARY

The invention provides a surgical preparation applicator device comprising;

a) a pre-loaded container of surgical preparation liquid, the container having a body and a front closure which can open to allow passage of the liquid out of the container, b) an applicator body which includes a receiving structure in which the container is received, the container and the receiving structure being capable of relative movement between an initial relative position and an open relative position, the applicator body also comprising an opener structure for opening the front closure of the container when the container is moved to the open relative position, and c) a deformable, liquid-permeable applicator pad, the applicator body defining a flow path between the container and the applicator pad, the device further comprising at least one of the following separate and independent proposals, which may be combined.

In a first aspect, we propose to provide a pre-loaded container comprising a plurality of separate chambers. The container has a front end, and each chamber has a front opening at the front end of the container, with the front closure closing off each front opening, and each chamber is opened by the opener structure when the container is moved to the open position. The chambers may contain different component liquids, which are mixed within the applicator body when the front closure is opened. This configuration allows the chambers to be filled simultaneously which allows for quicker filling of the chambers (which may save cost). It may also result in more reliable mixing of the components, which are released simultaneously.

The plural chambers are defined by the container body, which comprises a perimeter wall and at least one internal or dividing wall within the container. The front openings of chambers in the container are defined by these walls, each of which has a front edge meeting, contacting, welded or otherwise bonded to the front closure.

The opener structure may comprise at least one rearward projection, facing towards the front closure. There may be separate rearward projections for opening each of the plurality of chambers. The opener structure provides clearance for the internal wall when the container is in the open relative position. A guide mechanism may be provided to ensure that the internal wall(s) move into the clearance when the container is moved into the open relative position. This guide mechanism may comprise a protrusion on one of the exterior wall of the container and the receiving structure of the applicator body, which engages a channel on the other of the exterior wall of the container and the receiving structure of the applicator body. Providing the protrusion on the exterior wall of the applicator body, and the channel in the receiving structure of the applicator body may be simpler and preferable, as it will not affect the container volume.

The front closure may be a film, foil or other layer that is cut, broken or ruptured, a frangible part which is broken away, or a displaceable wall part such as a partition or plug which can be moved out of its position. Where the front closure is a film, foil or other layer that is cut, broken or ruptured, the front closure may be welded or otherwise bonded to the body of the container. The front closure is welded to the front edge of the walls which form the container body. As an internal wall is present, there is a larger surface area which is welded, and a stronger seal is formed. Alternatively, a bonding agent may be used between the body of the container and the front closure. This bonding agent is applied to the front edge of the walls which form the container body. As an internal wall is present, the bonding agent may be applied to a larger surface area, resulting in a stronger bond. A stronger seal or bond is advantageous if vacuum is applied during sterilization of the device.

There may be two separate chambers in the container. At least one of the chambers may contain an antiseptic agent. This may be an antimicrobial agent. Other suitable additives such as cleaning agents, liquid carriers, solvents and the like may be may be provided in at least one of the chambers. Each chamber may contain more than one of the above listed options.

One chamber may contain an antimicrobial agent, and the other another an antiseptic agent or solvent. Chlorhexidine gluconate is a preferred antimicrobial agent. Other antiseptic agents that may be used include alcohols, preferably isopropyl alcohol. One chamber may contain an antimicrobial agent e.g. in aqueous form, and the other an alcohol. These may be aqueous chlorhexidine gluconate and isopropyl alcohol.

The chambers may be arranged as radial sectors. In a device with two chambers, the internal wall may bisect the container at the front edge, and extend throughout the depth (length) of the container. This may define two chambers of equal volume that are arranged side-by-side. Alternatively the internal wall may form an inner chamber, with a second, outer chamber extending at least partially around its periphery. The inner chamber may be cylindrical, contained entirely within a second cylindrical, outer chamber, having an annular cross-section. Two chambers may be arranged in a number of other configurations. The chambers are preferably elongate in the longitudinal direction.

The component liquids are mixed in the applicator body as they pass along the flow path. This may be promoted by incorporating one or more flow-rate-limiting obstructions, holes, tubes, or other structures in the applicator body. Where more than one flow-rate-limiting structure is present, the flow rate through each structure may be less than the flow rate through the preceding structure in the flow path. The applicator body may provide compartments along the flow path which act as temporary reservoirs for the liquid as it passes from the container to the applicator pad. The limited flow rate out of each reservoir causes a build up of liquid in the reservoir, resulting in mixing. Turbulence through each flow-rate-limiting structure also increases mixing.

Drainage holes may be provided in the reservoirs where necessary to ensure that all liquid to be applied passes through to the applicator pad.

A second aspect, which is a separate and independent proposal but can be combined with any other proposal herein, relates to the opener structure.

Where the front closure is a film, foil or other layer that is cut, broken, or ruptured the opener structure may comprise one or more rearward projections facing towards the front closure and which break through it when the container is pushed forward. The opener structure may comprise a cutter projection arranged to cut through the closure layer. The opener structure may comprise a cutter, and a following or adjacent sweeper element positioned to push a cut section of the front closure out of the flow path to facilitate easy escape for the component liquids.

The sweeper element may be configured to engage the cut section after the cutting action is complete. It may meet, contact of form part of the cutter. However, it is preferably a separate element, spaced laterally from the cutter. It may be a rearward projection e.g. in the form of a rod, plate or tongue, flat or curved in plan.

The cutter may be a multi-pointed cutter, comprising a plurality of teeth arranged to cut through the front closure. The teeth of the multi-pointed cutter may be angled relative to the front closure, such that each tooth first interacts with the front closure in a point contact, piercing the front closure, and then cuts the front closure in a shearing action as the container is moved further towards the teeth.

The teeth of the multi-pointed cutter may be staggered, such that not all teeth interact with the front closure simultaneously, thereby increasing the pressure applied by each tooth when piercing. Preferably plural teeth are distributed along an edge of the cutter which extends obliquely to the front closure, so that the edge passes progressively through the plane of the closure as container and cutter are pushed together.

The teeth may be staggered such that within the profile of the cutter, there is a tooth or several teeth at a maximum or leading point, with a symmetric and even decrease in the cutter profile either side of the maximum, and with teeth arranged along the entire upper edge of the profile.

The teeth of the multi-pointed cutter may be arranged to cut through the front closure around all or part of the perimeter of each container chamber. This maximises the cross sectional area of the flow path. Further, the required pressure needed to pierce the front closure is smallest close to the seal or bond it forms with the container body, as the front closure bows least at this position. Thus, the cutter may be shaped to be complementary with the shape of the interior wall of the container where the closure is to be broken, e.g. formed (in plan) in an arc.

The teeth of the multi-pointed cutter may be configured such that they do not cut around the entire perimeter of the container chamber, leaving an uncut portion. Where a sweeper element is present, it may be positioned to engage the cut section proximal to the uncut portion. The profile of the sweeper element may be complementary with the shape of the interior wall of the container at the uncut portion, and positioned to engage the cut section of the front closure at this point, thereby pushing the cut section of the front closure so that it is lies along the interior wall. This maximises the flow path cross sectional area.

In the applicator of the first aspect with a plurality of chambers, the opener structure may comprise a separate cutter for opening each separate chamber. A sweeper element may also be provided for each separate chamber. Each cutter may embody any of the above listed proposals. Clearance is provided between the cutters for the internal wall(s) of the container body when the container is moved into the open position. A guide mechanism or structure may be provided to ensure that the internal wall(s) move into the clearance when the container is moved to the opened position. This guide mechanism may comprise a protrusion on one of the exterior wall of the container and the receiving structure of the applicator body, which engages a channel on the other of the exterior wall of the container and the receiving structure of the applicator body. The volume of the container may be important, and therefore it may be simpler and preferable to provide the protrusion on the exterior wall of the applicator body, and the channel in the receiving structure of the applicator body.

A third aspect, which is a separate and independent proposal but can be combined with any other proposal herein, relates to the applicator pad. The applicator pad may be configured so that liquid can be applied from multiple faces of the applicator pad. Holes in the applicator body allow passage of liquid into the applicator pad, the holes being differently and selectively sized to improve distribution of liquid throughout the pad. These holes may be configured to achieve approximately even saturation throughout the pad.

The applicator pad may have two opposing application faces. The faces may be parallel, or there may be an angle between them. This angle may be up to approximately 45°, preferably up to approximately 30°, more preferably up to approximately 10°. Liquid can be applied to two surfaces simultaneously (as may be required, for example, under an armpit, behind the knee or between fingers). The angle between the application faces may be selected depending on the application site. In these cases, the applicator pad is attached at an edge to the applicator body, such that both faces of the applicator pad can both be used in application of the liquid.

A rigid tongue may be provided which extends from the applicator body into the applicator pad. This serves to limit distortion of the applicator pad, and/or movement of the pad relative to the body.

The rigid tongue may include an elongate tube, which forms part of the flow path. Holes in the elongate tube allow passage of liquid into the applicator pad in use. These holes are selectively positioned and sized to improve distribution of liquid through the device. Ideally, an approximate even saturation throughout the pad is achieved.

The applicator body may have a longitudinal axis, and the angle between this axis and one of the application surfaces is less than 180°, preferably less than about 160°, preferably less than about 140°, and more than about 90°, preferably more than about 110°, preferably more than about 130°, most preferably about 135° allowing downward flow of the liquid from the container in use. If the angle is too large, the user's hand may be too close to the patient's skin, which compromises sterility. If the angle is too small, the applicator body may obstruct use of one of the application surfaces.

The liquid flows down to the applicator pad under the influence of gravity. The device is held in use to allow downward flow. This is a preferred orientation for the device, and defines the two application surfaces as an upper surface and a lower surface. A grip comprising ribbing is provided as an integral part of the applicator body, and the grip is positioned to encourage the user to hold the device in the preferred orientation. In such embodiments which have a preferred orientation, the elongate tube may have upper holes which communicate with the upper face of the applicator pad, and lower holes which communicate with the lower face of the applicator pad, the upper holes having a larger cross section than the lower holes.

The flow rate through the holes allowing passage of liquid to the applicator pad may be the limiting flow rate. The ratio of the area of the upper holes to the ratio of the area of the lower holes may be from about 1.5:1 to 4:1, preferably about 2:1 to 3:1. This may depend on the viscosity of the liquid.

Where there is an angle between application faces the thickness of the applicator pad is not uniform. In such cases, the elongate tube may have holes which communicate with the thicker parts of the applicator pad, and holes which communicate with the thinner parts of the applicator pad, the holes which communicate with the thicker parts having a larger cross section that the holes which communicate with the thinner parts.

Other features which may be included in combination with any of the above proposals are described and explained below.

The applicator body may provide a mechanism for preventing accidental movement of the pre-loaded container to the open position. This mechanism may comprise a resiliently deformable resistive element, which is overcome through application of a force to the container. Where a channel is provided in the receiving structure of the applicator body for engaging a protrusion on the exterior wall of the pre-loaded container, the resistive element may be a lip at one end of the channel, the lip having to be deformed through application of a force in order to engage the protrusion with the channel. Where a force is required to overcome the resistive element, the force may also be sufficient to move the container into the open position.

The entire device may be subject to sterilization procedures. These may use vacuum conditions.

Where vacuum conditions are used in sterilization, the front closure must be tightly welded, bound or otherwise attached to the body of the pre-loaded container in order to survive the vacuum. A stronger seal or bond may be achievable through use of the multi-chamber system in the pre-loaded container because the surface contact area is increased due to the internal walls between chambers. Further increase in the contact surface area can be achieved through providing castellations or lateral protrusions on the walls of the body which contact the front closure.

It is also desirable for the amount of air in the container chambers before opening to be minimised, thereby preventing bowing of the front closure under vacuum conditions. The chamber volumes may be altered in order to achieve this. Space filling webs may be employed to reduce the chamber volume. The front facing edges of any space filling webs may be spaced from the front opening of the container chamber, and these edges may be angled relative to the front opening, so as to prevent splash-back of liquid as the chamber is filled. Alternatively, the space filling webs may extend to contact the front closure. They may then act in the same manner as the castellations or lateral protrusions described above.

In sterilization procedures, sterilizing gas may be used. It is important that the gas can access all surfaces of the applicator that are not internal to the container. (Such gases can damage the components of the liquid to be applied, and so do not access the inside of the container.) A space may be provided between the receiving structure of the applicator body and the container to allow free flow of the sterilizing gases. In such embodiments, stabilising structures may be provided to ensure that the container moves into the open position correctly. It may also be desirable to prevent passage of the component parts of the liquid to be applied through this space. In these cases, the stabilising structures may be one or more ribs, provided either on the outside of the container or the inside of the applicator body, the ribs closing the space between the applicator body and the container. In order to maintain free flow of the sterilizing gases, each rib may have one or more small gaps provided in it, the gaps being sufficiently small that the surface tension of the treatment liquids acts to minimise the through-flow or of treatment liquid after the container is moved to the open position. Where there is more than one rib, the small gaps in adjacent ribs may be staggered to further minimise through-flow of liquid.

Any spaces or gaps provided to allow sterilizing gases to access all surfaces of the applicator that are not internal to the container, also act as air vents in use. Alternative or additional vents may also be provided in the applicator body. The vents ensure that an equal air pressure is maintained throughout the applicator, ensuring a smooth flow through each flow rate limiting part, and ensuring even mixing.

The sterilizing gases may be invasive substances, such as ethylene oxide. They should not contact the component parts of the liquid to be applied. The walls of the container are made of a material that is thick enough to prevent ingress of the sterilizing substance. Polyolefin walls for the pre-loaded container body are preferred (as they are cheap), with polypropylene most preferred. Container walls at least 2 mm thick are generally preferred to prevent contamination of the liquids.

The front closure is preferably a film, foil or other layer that is cut, broken or ruptured. Preferred front closures may be aluminium/polyester/polypropylene composites, or more preferably, aluminium/polypropylene composites.

BRIEF DESCRIPTION OF THE DRAWINGS

These proposals are now illustrated by description of an example, with reference to the accompanying drawings in which.

DESCRIPTION OF THE SELECTED EMBODIMENTS

Figure 1:
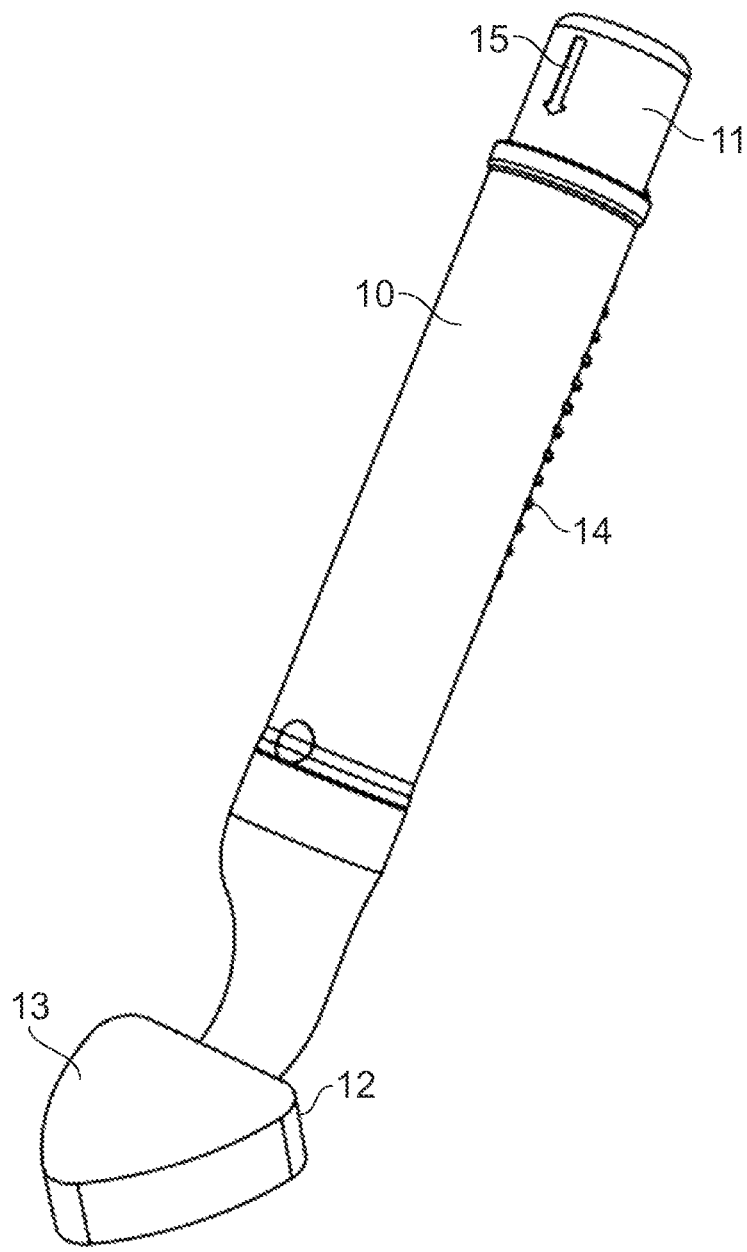
FIG. 1 is a perspective view of a surgical prep applicator embodying our proposals.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The applicator shown in FIG. 1 has an applicator body 10, and a cylindrical pre-loaded container 11. The applicator body is made from polypropylene. It is attached to the rear edge 12 of an approximately planar applicator pad 13. The pad is a polyurethane sponge. It has a rounded triangular shape. The pad has two opposing faces for application of liquid.

The applicator body extends outwardly and upwardly from the applicator pad. The angle between the upper application surface and the longitudinal axis of the cylindrical container is about 135°. A grip 14 is provided on the applicator body. This is positioned to encourage the user to hold the device in the orientation which allows downward flow of the component liquids. An arrow marker 15 is provided on the container body to aid correct insertion into the receiving structure 20 of the applicator body 10.

Figure 4:
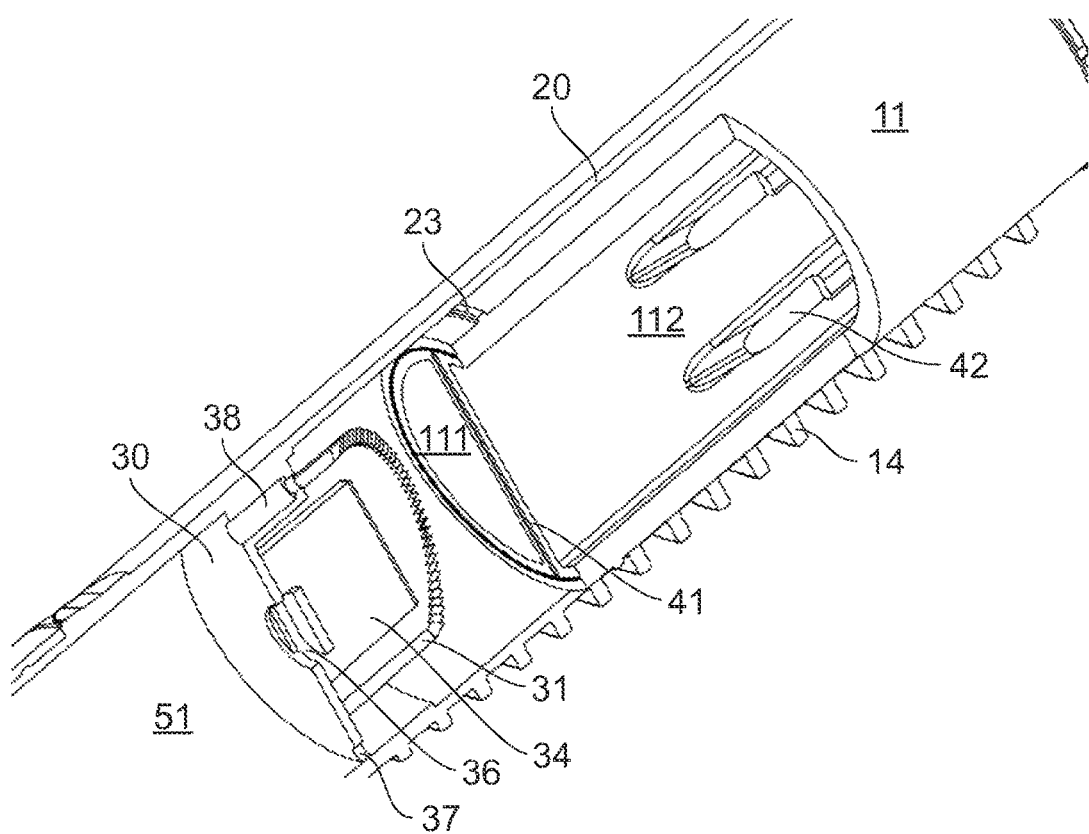
FIG. 4 is a partial sectional elevation like FIG. 3B extended to show the container interior, and with the front closure not shown.
Figure 5A:
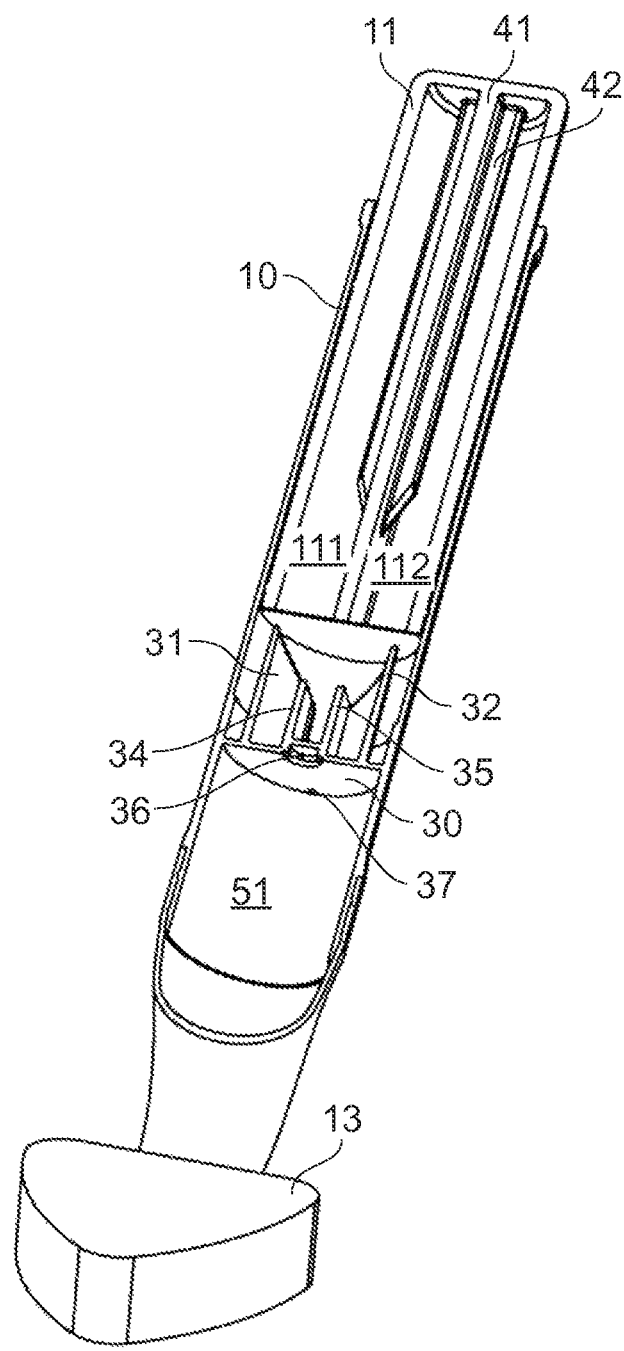
FIG. 5A is a sectional elevation through the applicator, at right angles to the FIG. 4 section and showing all the container interior.
Figure 5B:
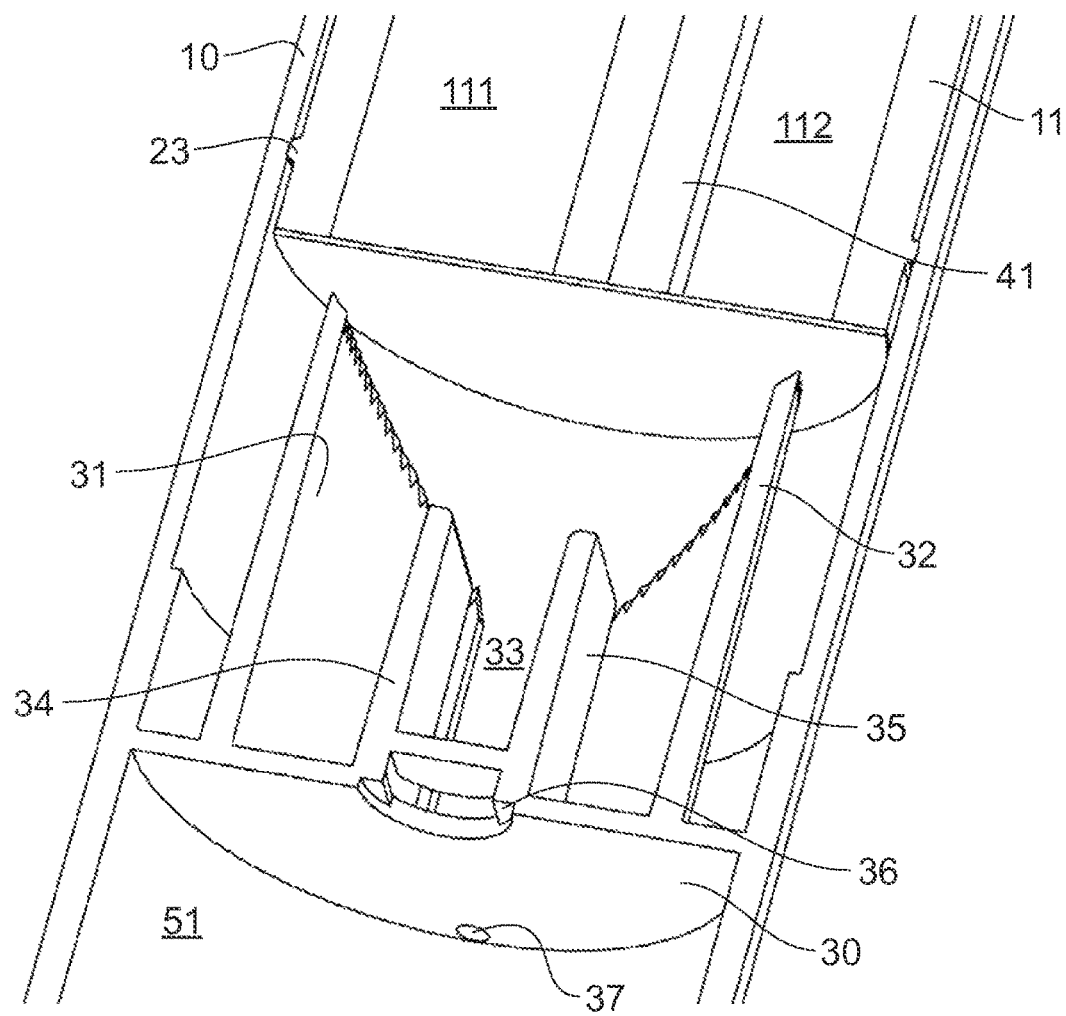
FIG. 5B is an enlarged sectional view of the closure and cutter as seen in FIG. 5A.

The cylindrical container 11 has two liquid-containing chambers 111,112 separated within the container by an integral internal wall 41 shown in FIG. 4. The walls of the container, including the internal wall 41, are made from polypropylene, and are 2.5 mm thick. Each of the chambers 111,112 is semi-circular in cross section. Both have an equal cross section. Each chamber holds 13 ml of liquid when full. One chamber contains an antimicrobial agent, such as aqueous chlorhexidine gluconate, and the other contains an antiseptic agent such as isopropyl alcohol. The chambers are closed with a foil closure 22, which is an aluminium/polypropylene composite. The foil closure 22 may be welded to the container body or attached using a bonding agent, which is applied to the front edge of the perimeter and internal walls. If a bonding agent is used, a cyanoacrylate bonding agent is preferred.

As shown in FIG. 4, the upper end of the applicator body 10 forms a hollow tube 20 which receives the cylindrical container 11. An integral partition 30 in the applicator body supports a cutter 21, the cutter being for engagement with the foil closure 22 of the container. A partition hole 36 in the centre of the partition allows passage of liquid into the lower end of the applicator body.

The cross sectional area of the partition hole 36 is less than the cross section of the cut foil closure. The flow rate through partition hole 36 is therefore less than the flow rate out of the container chambers. The partition 30 therefore dams a temporary reservoir in the applicator body, and the component liquids are mixed in this reservoir. Turbulent flow through partition hole 36 also mixes the component liquids.

A drain 37 is included at the lowest point of the partition 30 so ensure that all liquid flows to the applicator sponge.

Figure 6:
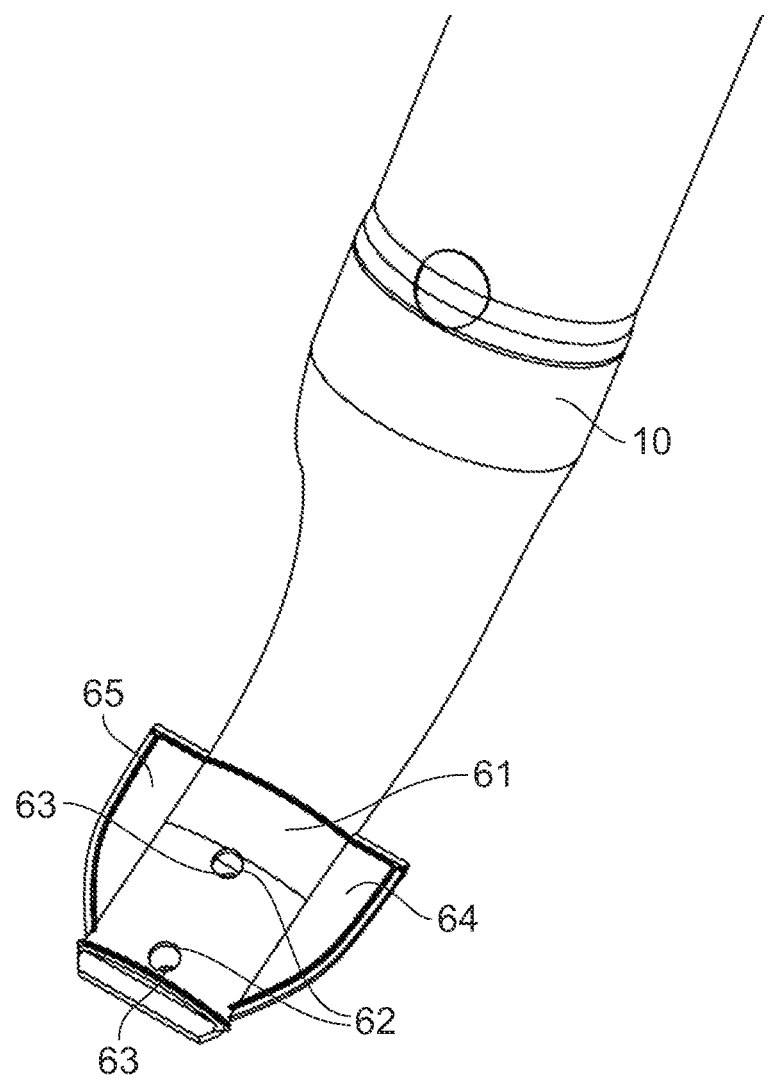
FIG. 6 is an enlarged view showing body part to support the applicator pad, the applicator pad not being shown.

The lower end of the applicator body defines a cavity 51 immediately below the partition 36. This cavity tapers to an elongate tube 61 (shown in FIG. 6) which extends into the applicator sponge. Upper holes 62 and lower holes 63 allow passage of liquid into the upper and lower parts of the sponge respectively.

Fins 64,65 project outwardly from the edges of the elongate tube 61 into the applicator sponge. These stabilise the form of the sponge and prevent excessive distortion and movement.

The flow rate through upper holes 62 and lower holes 63 is less than that through partition hole 36. A second temporary reservoir is therefore formed in cavity 51. Further mixing occurs in this reservoir.

The upper holes 62 have a larger cross section than the lower holes 63. The holes are circular, and the upper holes have a diameter of 4 mm, the lower holes have a diameter of 2 mm. This improves distribution of liquid to the upper part of the sponge, countering the effect of gravity.

A vent 38 is present which helps to equalise pressure throughout the flow path, and in particular between the upper and lower ends of the applicator body, by allowing air to pass through the partition 30.

The cutter 21 comprises two semi-circular opposing arrays of teeth 31,32. The teeth are arranged along the upper edge of the cutter. The centre tooth/teeth on each cutter is/are closest to the foil closure. The distance between the front closure and the teeth increases symmetrically and evenly either side of the centre tooth/teeth. This means that the teeth do not all interact with the front closure at the same time. This increases the pressure applied by each piercing tooth The arrays of teeth are aligned to pierce the foil closure 22 adjacent to the perimeter walls of the container. Each tooth in the arrays is angled relative to the foil closure such that it initially interacts with the foil closure in a point contact. This allows the teeth to pierce the foil closure.

Gaps 33 are present between the ends of the opposing arrays to receive the internal wall 41 of the container 11 when the container is moved into the fully advanced open position.

Two sweeping projections 34,35 are present between the arrays of teeth 31,32. These push the cut foil portion out of the flow path. The sweeping projections and the arrays of teeth do not meet, to improve mixing of the component liquids. The sweeping projections are separated from each other by a gap which receives the internal wall 41, when the container is in the fully advanced open position. The sweeping projections are aligned to enter the container adjacent to the internal wall 41, and push the cut foil to lie along the internal wall 41. The sweeping projections are further from the foil closure than any of the teeth, and so engage the cut foil portion as the container moves towards the fully advanced open position, and after cutting is complete.

Figure 2A:
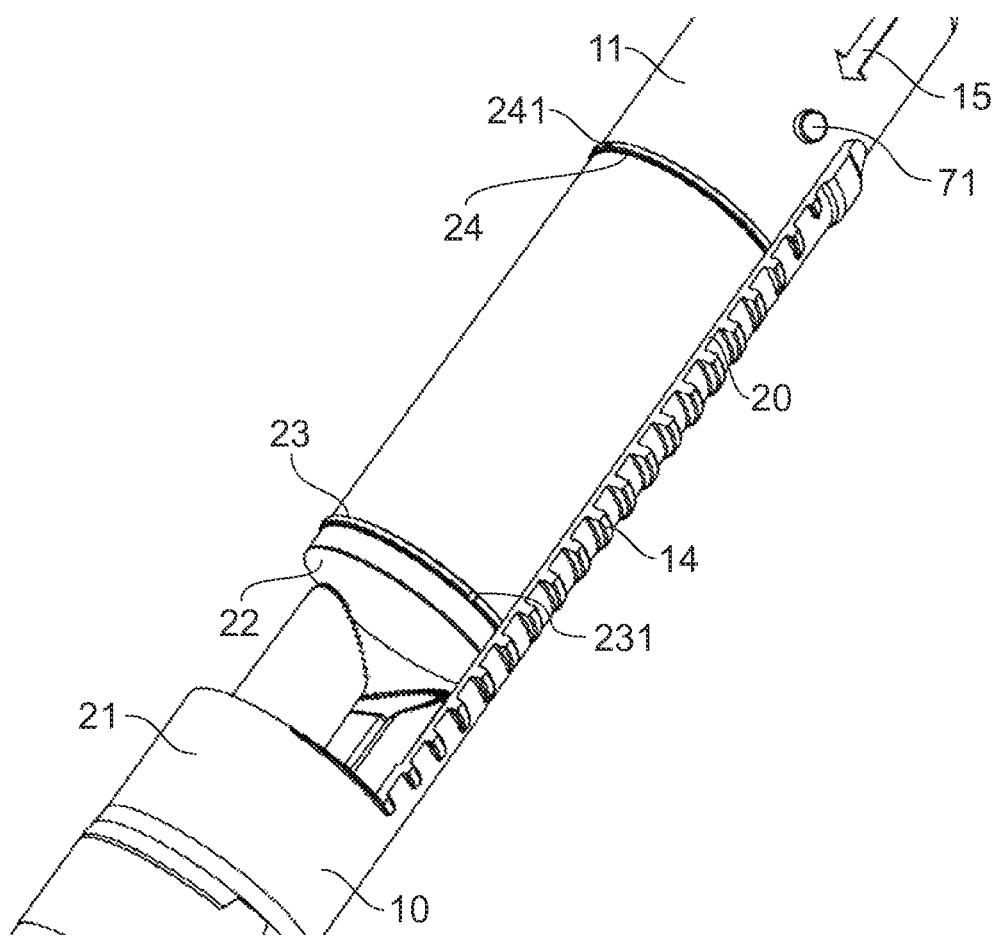
FIG. 2A is an enlarged perspective view of part of the same applicator, with part of the applicator body broken away.
Figure 2B:
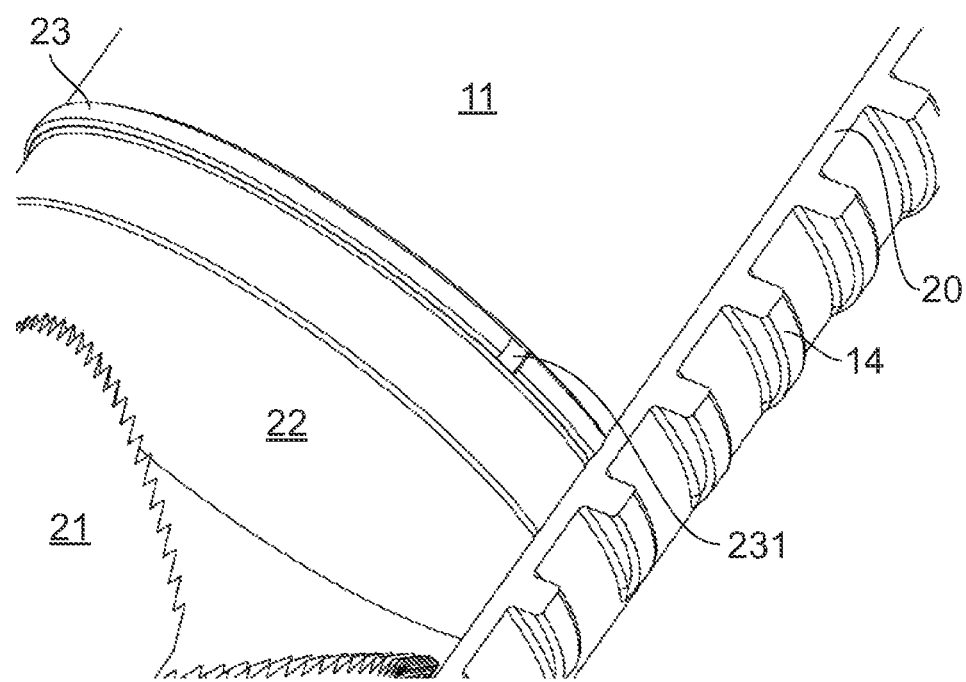
FIG. 2B is a further enlarged view of the same part, showing a lower support rib.
Figure 2C:
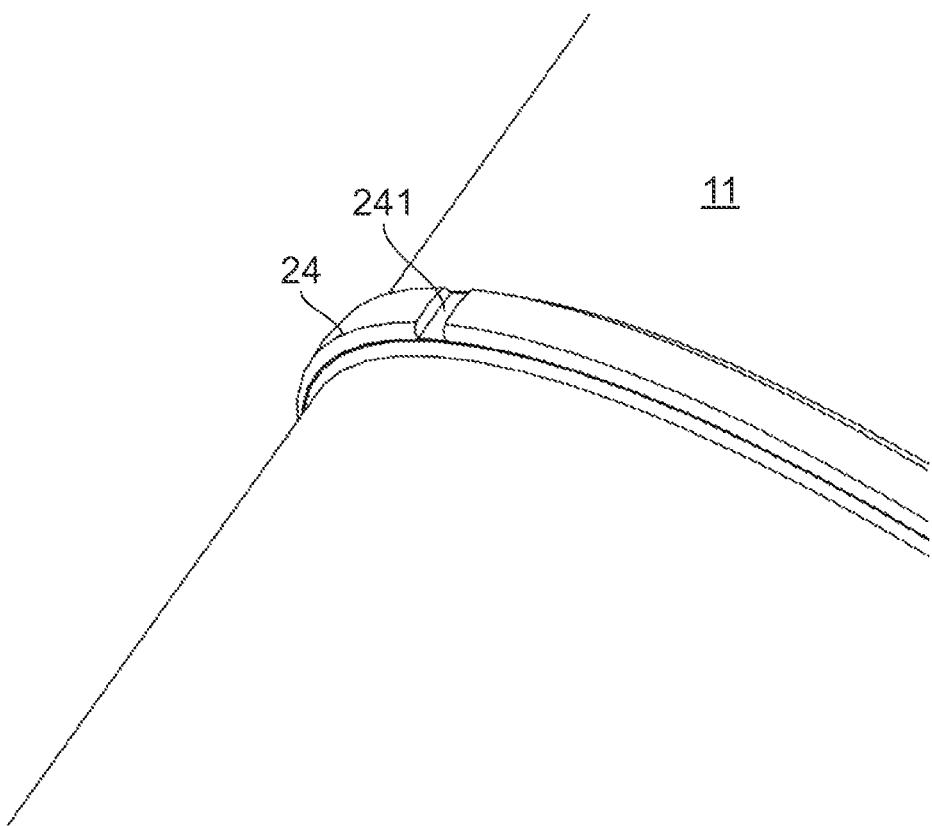
FIG. 2C is a still further enlarged view showing an upper support rib.
Figure 3A:
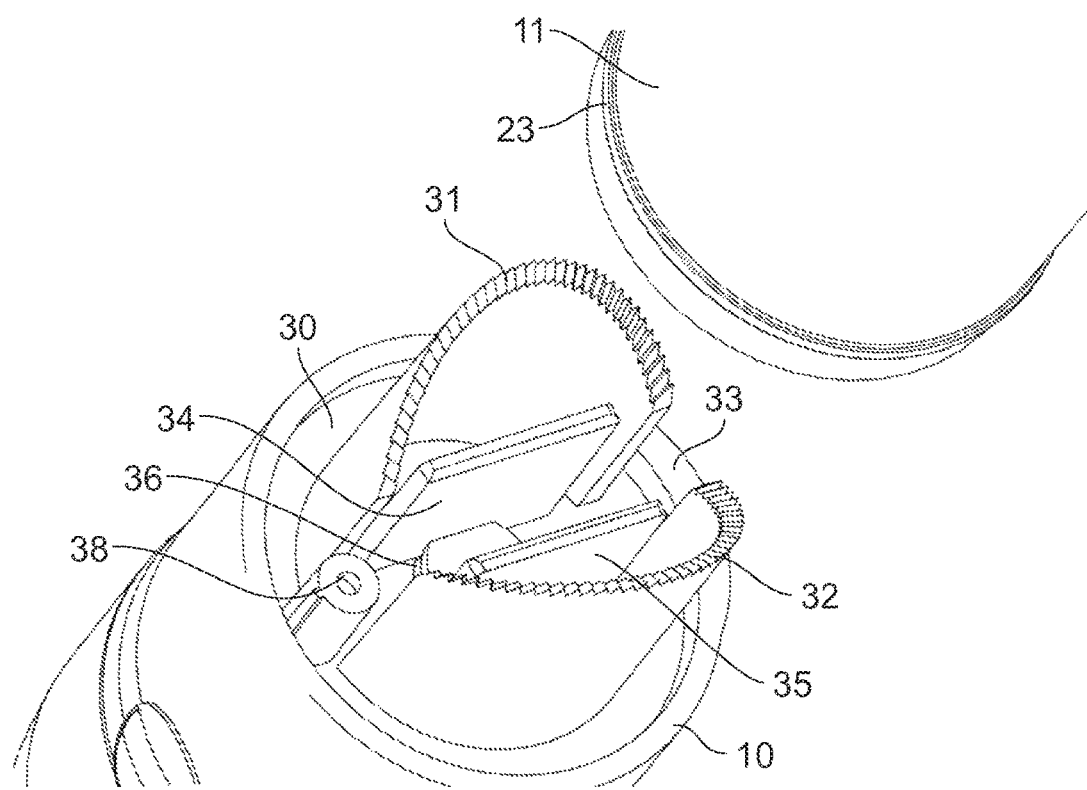
FIG. 3A is a top view of the applicator body, opened up to show a cutter.
Figure 3B:
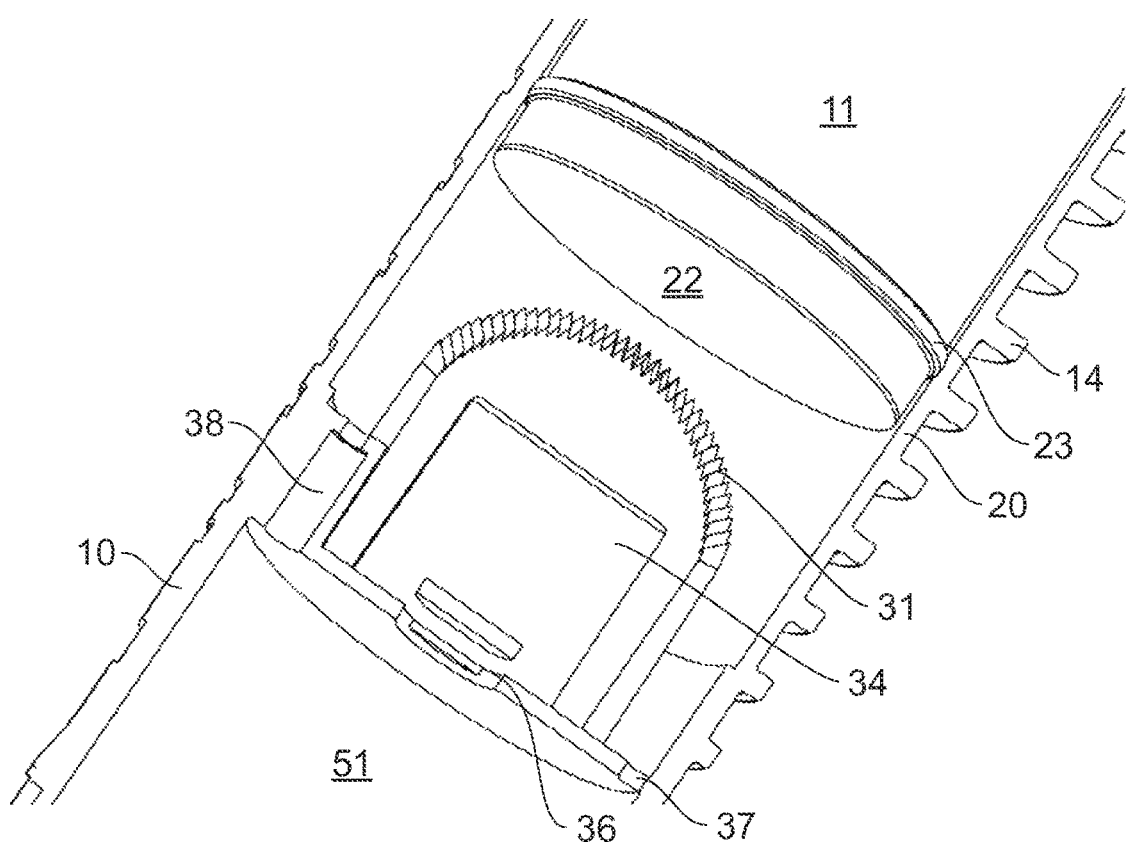
FIG. 3B is a part sectional elevation of the same part of applicator showing the cutter and the front closure of the container.

A small gap is present between the hollow tube 20 and the container 11. This allows sterilizing gases to flow freely around the device, and makes insertion of the container into the applicator body easier. As shown in FIG. 2, two ribs 23,24 are provided on the outside of the container which support the container within the hollow tube. The ribs also act to minimise leaking of any liquid between the container and the hollow tube, once the foil closure is opened. These ribs pass around the circumference of the container, except that a small gap 231,241 is provided in each rib. The gaps may be from approximately 0.3 mm, preferably approximately 0.5 mm to approximately 1.3 mm, preferably approximately 1 mm wide. The gaps are small enough that the surface tension of any liquids present minimises leaks through the gaps. The gaps in each rib 231,241 are offset relative to one another to further minimise leaks. The gaps also serve as vents to help equalise pressure throughout the flow path. They also allow sterilizing gases access to all surfaces of the device, other than the interior surfaces of the container.

As shown in FIG. 4, space-filling elongate bars 42 are provided in the chambers. The bars extend longitudinally along the internal wall 41. See also FIG. 8. The bars raise the liquid level of the filled chambers, and reduce the air volume in the sealed container. This is desirable in the vacuum conditions used during the sterilizing process. In some embodiments the bars do not extend to the front edge of the container, to prevent splashing of the component liquids during filling, and to provide clearance for the filling apparatus. The ends closest to the front opening may be bevelled to further reduce splashing. Alternatively the bars may extend up to the front edge of the container. This increases the area to which the foil closure 22 can be welded, or to which the bonding agent may be applied. This may result in a stronger seal or bond between the foil closure 22 and the container body.

Figure 7A:
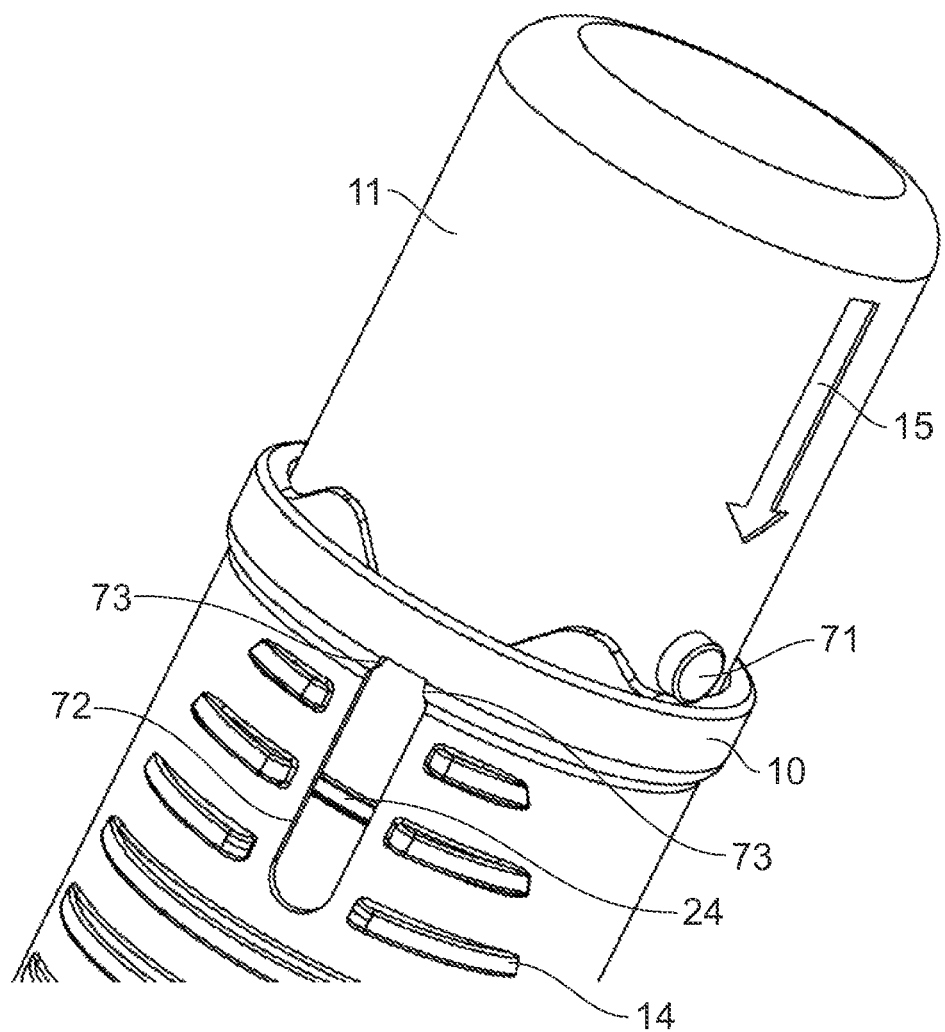
FIGS. 7A and 7B show a container guide bead and body channel in two positions.
Figure 7B:
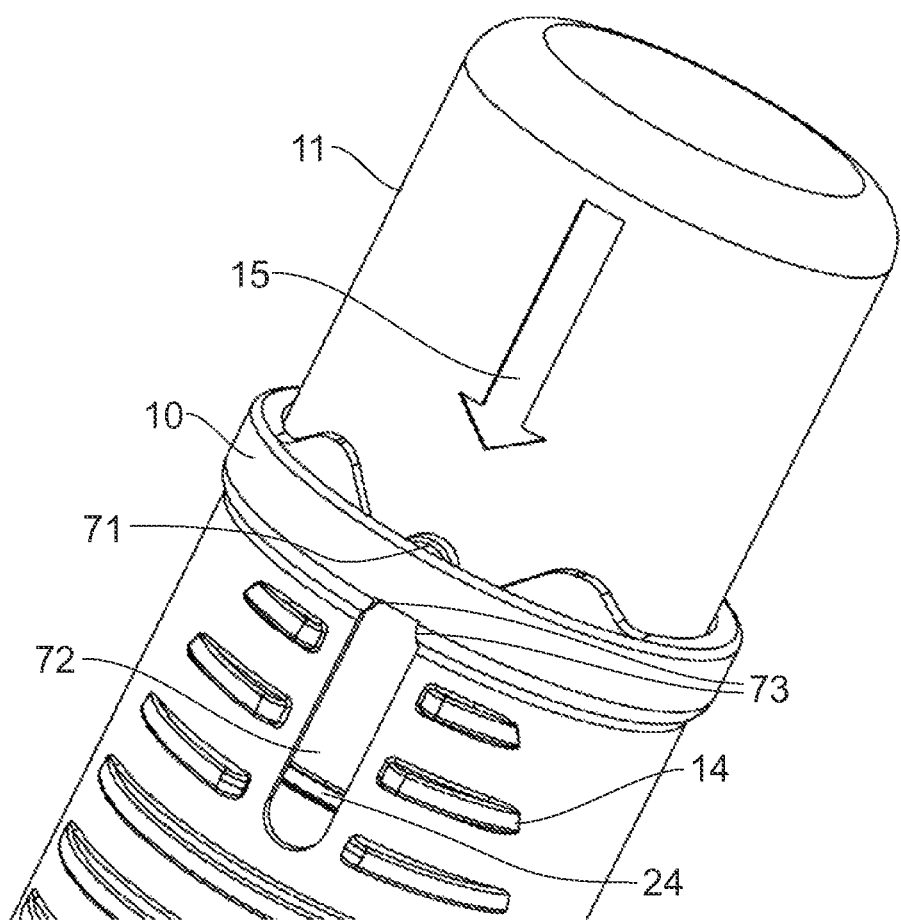
Figure 8:
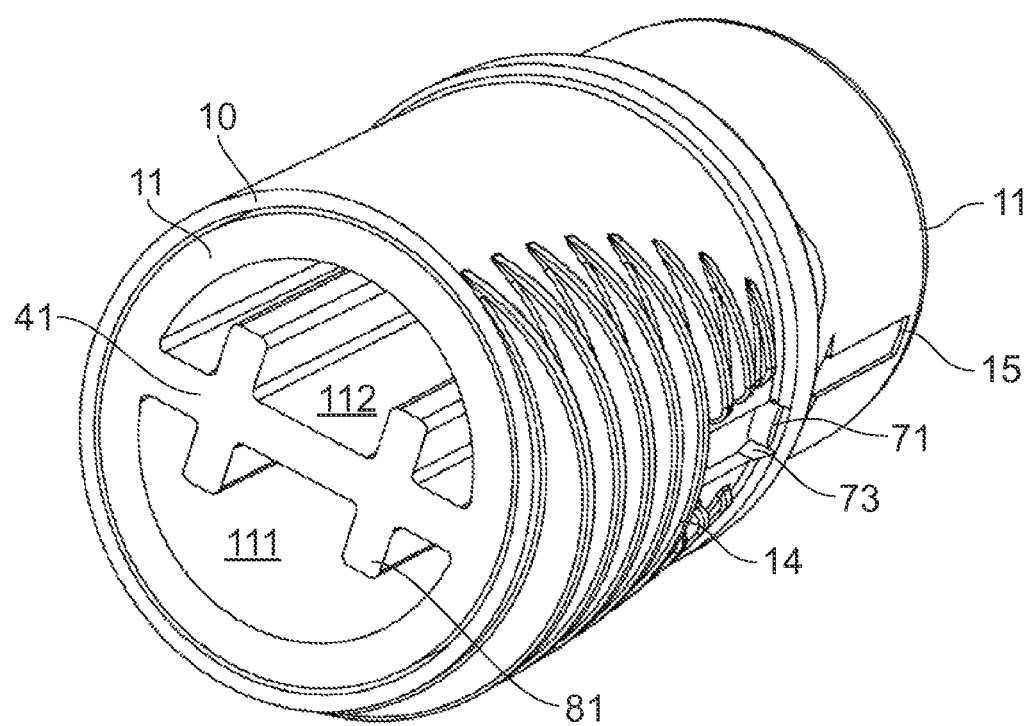
FIG. 8 is a sectional view of the invention.

As shown in FIGS. 7A, 7B and 8, a guide bead 71 is provided on outside of the container which engages a channel 72 formed in the applicator body. This ensures that the container is correctly oriented so that the cutter 21 engages the front closure 22 at the correct points, and that the internal wall 41 will be received by the gaps 33 as the container 11 is moved into the open position. One of the supporting ribs 24 is positioned on the container such that it is above the lowest point on the guide channel before the container is moved to the open position. This allows sterilization gases easier access to some areas of the device.

Inwardly projecting lips 73 are provided as part of the applicator body at the entrance to the channel 72. These narrow the channel and engage the guide bead 71. Force must be applied to the container push the guide bead 71 past the lips 73, and into the channel 72. The force needed to distort the lips 73 provides sufficient movement to the container that it moves to the open position and the cutter 21 is engaged.

The applicator body is made by injection moulding. The elongate tube 61 is formed with a hole in the end distal to the lower cavity 51. This hole is sealed using heat, after removal of the mould. The applicator sponge is sealed onto the applicator body using heat.

The pre-loaded container is also made by injection moulding. The chambers are then filled simultaneously. When filled, the liquid level is below the brim of the container chambers to prevent spillage during the filling and sealing process. The gap is at least four millimeters, e.g. 7 mm. It is however preferable to minimise this gap, thereby minimising air volume in the chambers, which is advantageous in the vacuum sterilization conditions.

The front closure is welded to the front edge of the container's perimeter and internal walls. Alternatively, a bonding agent may be applied to the front edge of the walls, which may be a cyanoacrylate. The foil closure portion is then applied. The container is inserted into the receiving structure of the applicator body. The device is sterilized using sterilizing gases, e.g. ethylene oxide, in vacuum conditions, e.g. at 80 mbar.

In use, the pre-loaded container is pushed from an initial position into the applicator body, to the open position. During the movement, the foil closure 22 first interacts with the sharp pointed corner of the closest tooth or teeth. This tooth, or these teeth, pierces the foil closure. As the container is moved further towards the open position, further sharp pointed corners of lower teeth serve to pierce the film. Teeth which have already pierced the foil closure cut the portion in a shear action.

As the pre-loaded container approaches the open position, the sweeping projections 34,35 engage the cut sections of the foil closure and pushes them upwards so that they lie along the internal wall 41 of the pre-loaded container, and largely out of the flow path.

The component liquids flow from the container downwards into the applicator body, and through the partition hole 36. As the flow rate through the hole is less than that out of the pre-loaded container, a temporary reservoir is formed. Mixing starts in this reservoir. Mixing also occurs as the liquids flow through partition hole 36.

The liquids follow the flow path into the lower cavity 51. Any liquid trapped by the partition 30 flows into the lower cavity through the drainage hole 37.

The flow path continues into elongate tube 61, and out through holes upper holes 62 and lower holes 63 into the applicator sponge. The flow rate through the upper and lower holes 62,63 is a limiting rate, so that a second temporary reservoir forms in the lower cavity 51. Further mixing occurs in this reservoir.

The applicator device is held in the orientation shown in FIG. 1. The holes in elongate tube 61 which communicate with the upper face of the applicator sponge are larger than the holes which communicate with the lower face of the applicator sponge. The sponge is approximately evenly saturated throughout.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A surgical preparation applicator device comprising:
a pre-loaded container of surgical preparation liquid, the container having a body and a front closure at a front end of the container which can open to allow passage of the liquid out of the container;
an applicator body which includes a receiving structure in which the container is received, the container and the receiving structure being capable of relative movement between an initial relative position and an open relative position, the applicator body also comprising an opener structure for opening the front closure of the container when the container is moved to the open relative position;
a deformable, liquid-permeable applicator pad, the applicator body defining a flow path between the container and the applicator pad; and
wherein the container has a plurality of separate chambers containing different component liquids of the surgical preparation liquid, each chamber having a front opening at the front end of the container, with the front closure closing off each front opening, whereby each chamber is opened by the opener structure when the container is moved to said open position, wherein said opener structure comprises cutters arranged to cut through the front closure which is a film, foil or other layer and wherein the opener structure comprises, for each cutter, an adjacent sweeper element positioned to push a cut section of the front closure out of the liquid flow path.

2. The surgical preparation applicator device of claim 1 wherein the sweeper element is a rearward projection in the form of a rod, plate or tongue.

3. A surgical preparation applicator device comprising:
a pre-loaded container of surgical preparation liquid, the container having a body and a front closure at a front end of the container which can open to allow passage of the liquid out of the container;
an applicator body which includes a receiving structure in which the container is received, the container and the receiving structure being capable of relative movement between an initial relative position and an open relative position, the applicator body also comprising an opener structure for opening the front closure of the container when the container is moved to the open relative position;
a deformable, liquid-permeable applicator pad, the applicator body defining a flow path between the container and the applicator pad; and
wherein the container has a plurality of separate chambers containing different component liquids of the surgical preparation liquid, each chamber having a front opening at the front end of the container, with the front closure closing off each front opening, whereby each chamber is opened by the opener structure when the container is moved to said open position, wherein said opener structure comprises cutters arranged to cut through the front closure which is a film, foil or other layer and wherein each cutter has a plurality of teeth which are distributed along the edge of the cutter which extends obliquely to the front closure, so that the edge passes progressively through a plane of the front closure as the container and each cutter are pushed together.

4. A surgical preparation applicator device comprising:
a pre-loaded container of surgical preparation liquid, the container having a body and a front closure at a front end of the container which can open to allow passage of the liquid out of the container;
an applicator body which includes a receiving structure in which the container is received, the container and the receiving structure being capable of relative movement between an initial relative position and an open relative position, the applicator body also comprising an opener structure for opening the front closure of the container when the container is moved to the open relative position;
a deformable, liquid-permeable applicator pad, the applicator body defining a flow path between the container and the applicator pad; and
wherein the container has a plurality of separate chambers containing different component liquids of the surgical preparation liquid, each chamber having a front opening at the front end of the container, with the front closure closing off each front opening, whereby each chamber is opened by the opener structure when the container is moved to said open position, wherein the opener structure comprises a separate cutter for each chamber, and for each said cutter an adjacent sweeper element to push a cut section of the front closure out of the liquid flow path for each chamber, clearance being provided between the cutters for an internal wall of the container body separating the chambers, when the container is moved to said open position.

5. The surgical preparation applicator device of claim 4 which further includes a guide mechanism to ensure that said internal wall moves into said clearance between the cutters, the guide mechanism comprising a protrusion on one of the exterior wall of the container and the receiving structure of the applicator body, said protrusion engaging a channel on the other of the exterior wall of the container and the receiving structure of the applicator body.

6. A surgical preparation applicator device comprising:
a pre-loaded container of surgical preparation liquid, the container having a body and a front closure at a front end of the container which can open to allow passage of the liquid out of the container;
an applicator body which includes a receiving structure in which the container is received, the container and the receiving structure being capable of relative movement between an initial relative position and an open relative position, the applicator body also comprising an opener structure for opening the front closure of the container when the container is moved to the open relative position;
a deformable, liquid-permeable applicator pad, the applicator body defining a flow path between the container and the applicator pad; and
wherein the container has a plurality of separate chambers containing different component liquids of the surgical preparation liquid, each chamber having a front opening at the front end of the container, with the front closure closing off each front opening, whereby each chamber is opened by the opener structure when the container is moved to said open position, wherein the applicator pad has two oppositely-directed application faces, and the applicator body has a rigid tongue incorporating a tube which is part of the flow path, which extends into the applicator pad and has respective holes for supplying liquid from the flow path to the respective application faces of the applicator pad, and wherein said faces of the applicator pad are an upper face and a lower face, said tube has upper holes which communicate with the upper face of the applicator pad and lower holes which communicate with the lower face of the applicator pad, and the upper holes have a larger cross-section than the lower holes.

7. A surgical preparation applicator device comprising:
a pre-loaded container of surgical preparation liquid, the container having a body and a front closure at a front end of the container which can open to allow passage of the liquid out of the container;
an applicator body which includes a receiving structure in which the container is received, the container and the receiving structure being capable of relative movement between an initial relative position and an open relative position, the applicator body also comprising an opener structure for opening the front closure of the container when the container is moved to the open relative position;
a deformable, liquid-permeable applicator pad, the applicator body defining a flow path between the container and the applicator pad; and
wherein the container has a plurality of separate chambers containing different component liquids of the surgical preparation liquid, each chamber having a front opening at the front end of the container, with the front closure closing off each front opening, whereby each chamber is opened by the opener structure when the container is moved to said open position, wherein a space is provided between the receiving structure of the applicator body and the container to allow flow of a sterilizing gas.

* * * * *